United States Patent
Yu (10) Patent No.: US 7,580,124 B2
(45) Date of Patent: *Aug. 25, 2009

(54) DUAL STAGE DEFECT REGION IDENTIFICATION AND DEFECT DETECTION METHOD AND APPARATUS

(75) Inventor: Zongqiang Yu, Santa Clara, CA (US)

(73) Assignee: KLA-Tencor Technologies Corp., Milpitas, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/974,033

(22) Filed: Oct. 10, 2007

(65) Prior Publication Data

US 2008/0106740 A1    May 8, 2008

Related U.S. Application Data

(63) Continuation of application No. 11/430,681, filed on May 8, 2006, now Pat. No. 7,295,301, which is a continuation of application No. 11/046,493, filed on Jan. 28, 2005, now Pat. No. 7,046,355, which is a continuation of application No. 10/191,765, filed on Jul. 9, 2002, now Pat. No. 6,850,321.

(51) Int. Cl.
*G01N 21/88* (2006.01)

(52) U.S. Cl. ............... 356/237.2; 356/237.4; 356/237.5; 356/394; 382/145

(58) Field of Classification Search ... 356/237.1–237.6, 356/239.1–239.3, 239.7–239.8, 394; 382/144–151, 382/154; 73/1.01, 1.89; 706/15–16, 23, 706/25

See application file for complete search history.

(56) References Cited

U.S. PATENT DOCUMENTS

| | | | |
|---|---|---|---|
| 3,851,951 | A | 12/1974 | Eveleth |
| 4,247,203 | A | 1/1981 | Levy |
| 4,579,455 | A | 4/1986 | Levy |
| 4,633,504 | A | 12/1986 | Wihl |
| 4,644,172 | A | 2/1987 | Sandland |
| 4,805,123 | A | 2/1989 | Specht |
| 4,926,489 | A | 5/1990 | Danielson |

(Continued)

OTHER PUBLICATIONS

Robert M. Haralick, et al,"Image Analysis Using Mathematical Morphology," IEEE Transactions on Pattern Analysis and Machine Intelligence, vol. PAMI-9, No. 4, Jul. 1987, pp. 332-350.

(Continued)

*Primary Examiner*—Sang Nguyen
(74) *Attorney, Agent, or Firm*—Smyrski Law Group, A.P.C.

(57) ABSTRACT

A method and apparatus for inspecting patterned substrates, such as photomasks, for unwanted particles and features occurring on the transmissive as well as pattern defects. A transmissive substrate is illuminated by a laser through an optical system comprised of a laser scanning system, individual transmitted and reflected light collection optics and detectors collect and generate signals representative of the light transmitted and reflected by the substrate. The defect identification of the substrate is performed using transmitted and reflected light signals from a baseline comparison between two specimens, or one specimen and a database representation, to form a calibration pixelated training set including a non-defective region. This calibration pixelated training set is compared to a transmitted-reflected plot map of the subject specimen to assess surface quality.

25 Claims, 9 Drawing Sheets

U.S. PATENT DOCUMENTS

| | | | |
|---|---|---|---|
| 5,563,702 A | 10/1996 | Emery | |
| 5,572,598 A | 11/1996 | Wihl | |
| 5,767,974 A | 6/1998 | Higashiguchi et al. | |
| 5,822,055 A | 10/1998 | Tsai et al. | |
| 5,838,433 A | 11/1998 | Hagiwara | |
| 5,850,467 A | 12/1998 | Matsui et al. | |
| 5,864,394 A * | 1/1999 | Jordan et al. | 356/237.2 |
| 5,995,219 A | 11/1999 | Tabata | |
| 6,052,478 A | 4/2000 | Wihl | |
| 6,282,309 B1 | 8/2001 | Emery | |
| 6,466,314 B1 | 10/2002 | Lehman | |
| 6,515,742 B1 * | 2/2003 | Ruprecht | 356/237.4 |
| 6,556,291 B2 | 4/2003 | Yonezawa | |
| 6,636,301 B1 | 10/2003 | Kvame | |
| 6,836,560 B2 | 12/2004 | Emery | |
| 6,850,321 B1 | 2/2005 | Yu | |
| 7,152,219 B2 * | 12/2006 | Pang | 716/19 |
| 7,274,813 B2 * | 9/2007 | Maeda et al. | 382/141 |

OTHER PUBLICATIONS

Anil K. Jain, "Image Analysis and Computer Vision, Fundamentals of Digital Image Processing," Chapter 9, (1989), pp. 384-389.

Masataka Shiba, et al., "Automatic Inspection of Contaminates on Reticles," SPIE vol. 470 Optical Microlithography III, (1984), pp. 233-240.

James A. Freeman, et al., "Neural Networks Algorithms, Applications, and Programming Techniques, Backpropagation," Chapter 3, (1992), pp. 89-125.

* cited by examiner

DUAL STAGE DEFECT REGION IDENTIFICATION AND DEFECT DETECTION METHOD AND APPARATUS

This application is a continuation of U.S. patent application Ser. No. 11/430,681, filed May 8, 2006, now U.S. Pat. No. 7,295,301 which is a continuation of U.S. patent application Ser. No. 11/046,493, filed Jan. 28, 2005, now U.S. Pat. No. 7,046,355, which is a continuation of U.S. patent application Ser. No. 10/191,765, filed Jul. 9, 2002, now U.S. Pat. No. 6,850,321, entitled, "Dual Stage Defect Region Identification and Defect Detection Method and Apparatus," all of which are hereby incorporated by reference.

BACKGROUND OF THE INVENTION

1. Field of the Invention

The present invention relates to methods and apparatus for inspecting the surface of a substrate such as reticles, photomasks, wafers and the like (hereafter referred to generally as photomasks). More specifically, the present invention relates to an optical inspection system and method for scanning specimens at a high speed and with a high degree of sensitivity.

2. Description of the Related Art

Integrated circuits are produced using photolithographic processes, which employ photomasks or reticles and a light source to project a circuit image onto a silicon wafer. Photomask surface defects are highly undesirable and adversely affect the resulting circuits. Defects can result from, but not limited to, a portion of the pattern being absent from an area where it is intended to be present, a portion of the pattern being present in an area where it is not intended to be, chemical stains or residues from the photomask manufacturing processes which cause an unintended localized modification of the light transmission property of the photomask, particulate contaminates such as dust, resist flakes, skin flakes, erosion of the photolithographic pattern due to electrostatic discharge, artifacts in the photomask substrate such as pits, scratches, and striations, and localized light transmission errors in the substrate or pattern layer. Since it is inevitable that defects will occur, these defects are preferably located and repaired prior to use. Blank substrates can also be inspected for defects prior to patterning.

Methods and apparatus for detecting defects have been available. For example, inspection systems and methods utilizing laser light are available to scan the surface of substrates such as photomasks, reticles and wafers. These laser inspection systems and methods generally include a laser source for emitting a laser beam, optics for focusing the laser beam to a scanning spot on the surface of the substrate, a stage for providing translational travel, collection optics for collecting either transmitted and/or reflected light, detectors for detecting either the transmitted and/or reflected light, sampling the signals at precise intervals and using this information to construct a virtual image of the substrate being inspected. By way of example, representative laser inspection systems are described in U.S. Pat. No. 5,563,702 to Emery et al., U.S. Pat. No. 5,737,072 to Emery et al., U.S. Pat. No. 5,572,598 to Wihl et al., and U.S. Pat. No. 6,052,478 to Wihl et al., each of which are incorporated herein by reference.

Although such systems work well, ongoing work in the area seeks to improve existing designs to enable higher degrees of sensitivity, increase the ability to classify and quantify defects, and to allow faster scanning speeds and higher throughput. As the complexity of integrated circuits has increased, the demands on the inspection of the integrated circuits have also increased. Both the need for resolving smaller defects and for inspecting larger areas have resulted in greater magnification requirements and greater speed requirements.

Various methods exist to perform detailed inspections of patterned masks or reticles. One inspection method is a die-to-die comparison which uses transmitted light to compare either two adjacent dies or a die to the CAD database of that die. These comparison-type inspection systems are quite expensive because they rely on pixel-by-pixel comparison of all the dies and, by necessity, rely on highly accurate methods of alignment between the two dies used at any one time for the comparison. Apart from their high costs, this method of inspection is also unable to detect particles on opaque parts of the reticle which have the tendency to subsequently migrate to parts that are transparent and then cause a defect on the wafer. One such die-to-die comparison method of inspection is described in U.S. Pat. Nos. 4,247,203 and 4,579,455, both by Levy et al.

The second method for inspecting patterned masks is restricted to locating particulate matter on the mask. This method makes use of the fact that light scatters when it strikes a particle. Unfortunately, the edges of the pattern also cause scattering and for that reason these systems are unreliable for the detection of particles smaller than one micrometer. Such systems are described in a paper entitled "Automatic Inspection of Contaminates on Reticles" by Masataka Shiba et al., *SPIE Vol.* 470 *Optical Microlithography III*, pages 233-240 (1984).

A third example of a system for performing photomask inspection is disclosed in U.S. Pat. No. 5,563,702 to David G. Emery, issued Oct. 8, 1996. The system disclosed therein acquires reflected images, in addition to transmitted images, to locate defects associated with contaminants, particles, films, or other unwanted materials. Since this system locates defects without reference or comparison to a description or image of the desired photomask pattern, it may in certain circumstances not locate defects outside of known boundaries, such as where the transmitted and reflected images differ from an expected amount by a threshold amount.

Specific types of photomasks called APSMs, or Alternating Phase Shift Masks, are typically designed with thickness variations in the glass or quartz which induce phase shift transitions between adjacent regions during photolithography. Phase defects can exist which are unwanted thickness variations created by phase etch process errors, and have similar optical image signatures during inspection. Hence APSM phase defects are difficult to distinguish from design phase features using the system shown in U.S. Pat. No. 5,563,702. Phase defects cannot be detected by this system without producing false defect readings on phase shift design features where no defects actually exist. However, the transmitted and reflected imaging capabilities and defect detection operators of this system can be useful to determine the presence of phase defects if all detected phase features are properly compared and contrasted to reference photomask image data, as in a die-to-die or die-to-database system.

The use of reflected light in combination with transmitted light may improve detection of phase defects. The difficulty with using reflected light is managing image artifacts, such as the bright chrome halos resulting from the removal of the antireflective chrome layer during quartz etching of phase shifters. Bright chrome halos may have variable widths resulting from second write level registration tolerances with intra-plate variations. These variations are not observable when solely using transmitted light inspection techniques.

Thus, in general, phase feature signals captured with brightfield transmitted light may vary widely depending on mask and defect characteristics, and phase feature signals captured in reflected light may be stronger. On the other hand, use of reflected light can be problematic in the presence of image artifacts such as bright chrome halos. Therefore, die-to-die or die-to-database photomask inspection with transmitted and reflected light may benefit from signal-to-noise enhancements as well as an enhanced ability to discern phase shift features and phase defects.

During inspection, different light sources can drastically affect the quality of the information received in the presence of certain types of defects. The phase defect signal in brightfield transmitted light can be substantially less than that of a similarly sized chrome defect, thereby complicating the ability to inspect the mask. The phase defect's signal depends on a variety of factors, including the height or phase angle of the phase defect, the depth of the phase shifters, and inspection system optical parameters.

Figure 3:
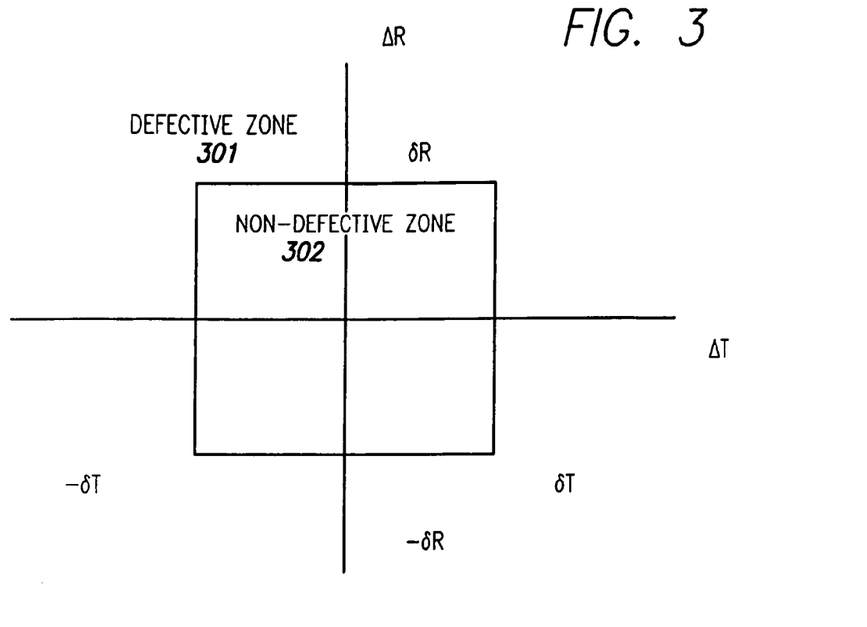
FIG. 3 illustrates a transmitted-reflected (ΔT-ΔR) plane including a constant threshold non-defective zone.

An alternate method employed for defect detection is an extension of the die-to-database comparison method, wherein the system compares two die with an identical design. The images employed may be either reflected or transmitted light energy images. One of the two die is called the reference die, and the other is called the test die. In this method, if the difference between the pixels of the reference die and the test die exceed a predetermined value, the pixel is marked defective. The transmitted threshold may be called $\delta T$, while the reflected threshold is $\delta R$. Performance of a defect detection algorithm may be viewed as a $\Delta T$-$\Delta R$ plane as illustrated in FIG. 3. From FIG. 3, $\Delta T$ represents the transmitted image difference between the test and reference dies, while $\Delta R$ is the reflected image difference between the test and reference dies. Previous methods have performed transmitted image detection independent from reflected image detection, where a defective zone is separated from a non-defective zone using constant thresholds as shown in FIG. 3. These previous methods employed constant thresholds for determining and quantifying defects. Non-defective zones used in the presence of constant thresholds have been found to be excessively large, resulting in declaring defects when no true defects exist, requiring additional post processing. A smaller non-defective zone is preferable, as it translates to higher defect detectability. In other words, if the non-defective zone of FIG. 3 is small, a higher probability that a defect will be located exists. However, decreasing the non-defective zone excessively may result in too many anomalies being classified as defects. In actuality, many errors between dies exist, including errors between test and reference dies. If the threshold is too small, a large number of false or nuisance defects will develop, taking a great deal of time to inspect, decreasing overall throughput.

One type of defect identification system and method is presented in pending U.S. patent application Ser. No. 09/991, 327, entitled "Advanced Phase Shift Inspection Method" to David G. Emery, filed on Nov. 9, 2001 and assigned to the assignee of the present invention. While the system disclosed therein provides for inspection of APSMs using transmitted and reflected light, certain defects may exist that may not be picked up by the Emery design. Further, the Emery design may require inspection of areas that are flagged as defective or potentially defective, potentially decreasing overall speed and throughput.

In view of the foregoing, there is a need for improved inspection techniques that provide for improved detectability while at the same time avoiding excess false and nuisance detections when scanning specific types of semiconductor specimens, such as APSM photomasks.

SUMMARY OF THE INVENTION

The present invention provides improved apparatus and methods for performing an inspection of a specimen, such as an APSM photomask.

In one aspect of the present invention, there is provided a method for inspecting a specimen, comprising performing a transmitted energy calibration inspection and a reflected energy calibration inspection of a plurality of calibration specimens, computing a training set based on the transmitted energy calibration inspection and reflected energy calibration inspection of the plurality of calibration specimens, performing a transmitted energy defect detection inspection and a reflected energy defect detection inspection of a plurality of specimens, computing a plot map based on the transmitted energy defect detection inspection and the reflected energy defect detection inspection of the plurality of specimens, and comparing the plot map to the training set to determine differences therebetween.

According to a second aspect of the present invention, there is provided a method for inspecting a specimen, comprising performing a transmitted energy calibration inspection and a reflected energy calibration inspection of a calibration specimen, computing a training set based on the transmitted energy inspection and reflected energy inspection of the calibration specimen and transmitted energy and reflected energy from a baseline specimen, performing a transmitted energy defect detection inspection and a reflected energy defect detection inspection of the specimen, computing a plot map based on the transmitted energy defect detection inspection and the reflected energy defect detection inspection of the specimen and transmitted energy and reflected energy from an alternate baseline specimen, and comparing the plot map to the training set to determine differences therebetween.

According to a third aspect of the present invention, there is provided a system for inspecting a specimen, comprising a training set table generator that generates a combined calibration transmitted energy and calibration reflected energy difference representation, and a defect detector that receives the combined calibration transmitted energy and calibration reflected energy difference representation and a transmitted and reflected energy representation of the specimen and determines the differences therebetween.

According to a fourth aspect of the present invention, there is provided a method for inspecting a specimen, comprising computing a training set based on a transmitted energy calibration inspection and reflected energy calibration inspection of at least one calibration specimen, computing a plot map based on a transmitted energy defect detection inspection and a reflected energy defect detection inspection of the specimen, and comparing the plot map to the training set to determine differences therebetween.

These and other objects and advantages of all of the aspects of the present invention will become apparent to those skilled in the art after having read the following detailed disclosure of the preferred embodiments illustrated in the following drawings.

BRIEF DESCRIPTION OF THE DRAWINGS

The present invention is illustrated by way of example, and not by way of limitation, in the figures of the accompanying drawings in which.

DETAILED DESCRIPTION OF THE INVENTION

The present invention will now be described in detail with reference to a few specific embodiments thereof and as illustrated in the accompanying drawings. In the following description, numerous specific details are set forth in order to provide a thorough understanding of the present invention. It will be apparent, however, to one skilled in the art, that the present invention may be practiced without some or all of these specific details. In other instances, well known process steps have not been described in detail in order not to unnecessarily obscure the present invention.

Figure 1:
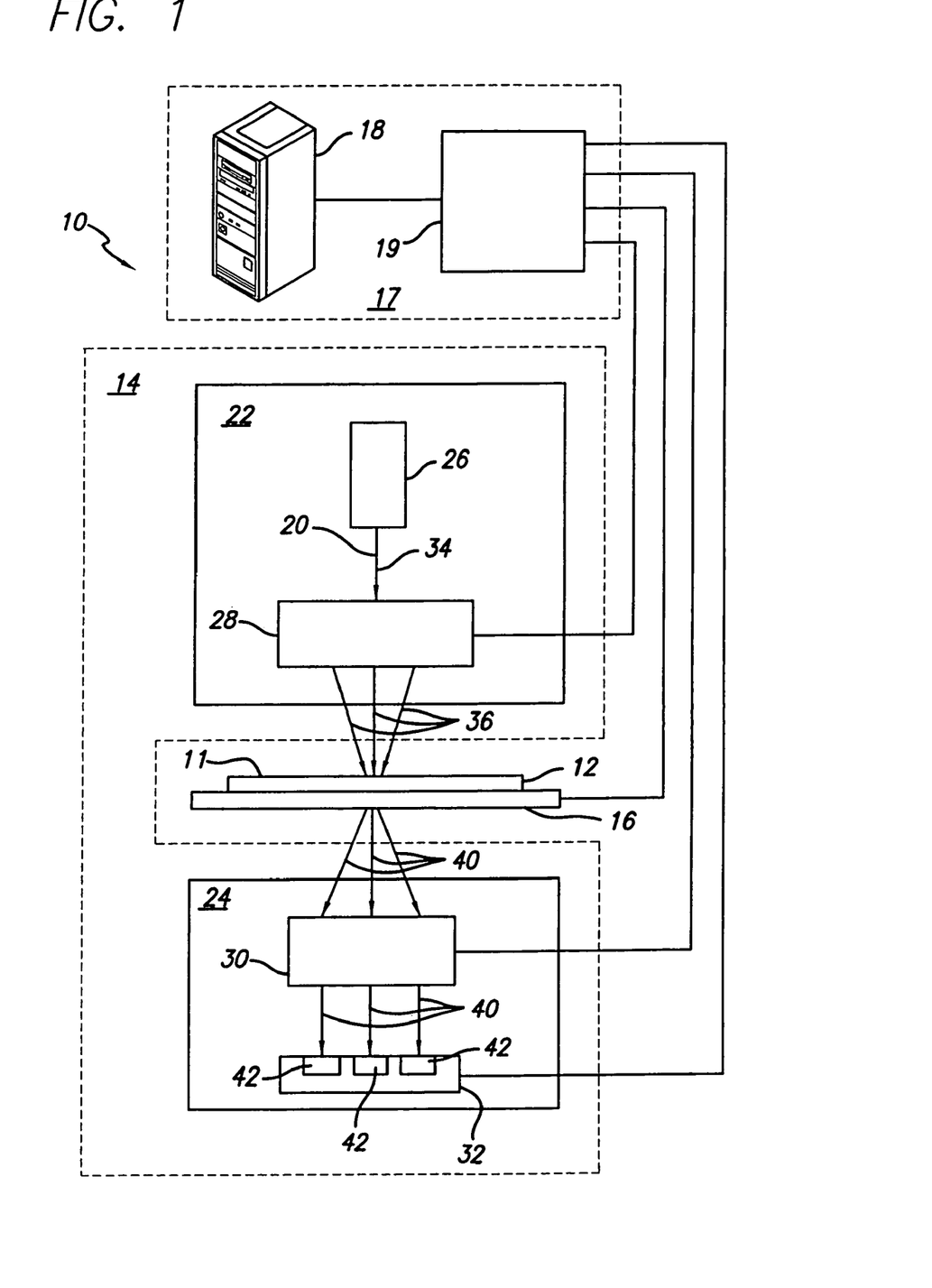
FIG. 1 is a simplified block diagram of an optical inspection system in accordance with one aspect of the present invention.

FIG. 1 is a simplified block diagram of an optical inspection system 10, in accordance with one aspect of the present invention. The optical inspection system 10 is arranged for inspecting a surface 11 of a substrate 12. The dimensions of various components are exaggerated to better illustrate the optical components of this embodiment. As shown, the optical inspection system 10 includes an optical assembly 14, a stage 16, and a control system 17. The optical assembly 14 generally includes at least a first optical arrangement 22 and a second optical arrangement 24. In general terms, the first optical arrangement 22 generates two or more beams incident on the substrate, and the second optical arrangement 24 detects two or more beams emanating from the sample as a result of the two or more incident beams. The first and second optical arrangement may be arranged in suitable manner in relation to each other. For example, the second optical arrangement 24 and the first optical arrangement 22 may both be arranged over the substrate surface 11 so that reflected beams resulting from incident beams generated by the first optical arrangement 22 may be detected by the second optical arrangement 24.

In the illustrated system, the first optical arrangement 22 is arranged for generating a plurality of scanning spots (not shown) along an optical axis 20. As should be appreciated, the scanning spots are used to scan the surface 11 of the substrate 12. On the other hand, the second optical arrangement 24 is arranged for collecting transmitted and/or reflected light that is produced by moving the scanning spots across the surface 11 of the substrate 12.

To elaborate further, the first optical arrangement 22 includes at least a light source 26 for emitting a light beam 34 and a first set of optical elements 28. The first set of optical elements 28 may be arranged to provide one or more optical capabilities including, but not limited to, separating the light beam 34 into a plurality of incident light beams 36, directing the plurality of incident light beams 36 to intersect with the surface 11 of the substrate 12, and focusing the plurality of incident light beams 36 to a plurality of scanning spots (not shown in FIG. 1) on the surface 11 of the substrate 12. The amount of first beams produced generally corresponds to the desired inspection speed. In one embodiment, the optical elements are arranged to separate the beam 34 into three incident light beams 36. By triplicating the beam, a wider scan is produced and therefore the resulting inspection speed is about three times faster than the speed produced for a non-triplicated single beam. Although only three light beams are shown, it should be understood that the number of separated light beams may vary according to the specific needs of each optical inspection system. For example, two beams may be used or four or more beams may be used. It should be noted, however, that the complexity of the optic elements is directly proportional to the number of beams produced.

Furthermore, the second optical arrangement 24 includes at least a second set of optical elements 30 and a light detecting arrangement 32. The second set of optical elements 30 are in the path of a plurality of collected light beams 40, which are formed after the plurality of incident light beams 36 intersect with the surface 11 of the substrate 12. The plurality of collected light beams 40 may result from transmitted light that passes through the substrate 12 and/or reflected light that is reflected off the surface 11 of the substrate 12. The second set of optical elements 30 are adapted for collecting the plurality of collected light beams 40 and for focusing the collected light beams 40 on the light detecting arrangement 32. The light detecting arrangement 32 is arranged for detecting the light intensity of the collected light beams 40, and more particularly for detecting changes in the intensity of light caused by the intersection of the plurality of incident light beams with the substrate. The light detecting arrangement 32 generally includes individual light detectors 42 that correspond to each of the second light beams 40. Furthermore, each of the detectors 42 is arranged for detecting the light intensity and for generating signals based on the detected light.

With regards to the stage 16, the stage 16 is arranged for moving the substrate 12 within a single plane (e.g., x & y directions) and relative to the optical axis 20, so that all or any selected part of the substrate surface 11 may be inspected by the scanning spots. In most embodiments, the stage 16 is arranged to move in a serpentine fashion. With regards to the control system 17, the control system 17 generally includes a control computer 18 and an electronic subsystem 19. Although not shown, the control system 17 may also include a keyboard for accepting operator inputs, a monitor for providing visual displays of the inspected substrate (e.g., defects), a database for storing reference information, and a recorder for recording the location of defects. As shown, the control computer 18 is coupled to the electronic subsystem 19 and the electronic subsystem 19 is coupled to various components of the optical inspection system 10, and more particularly to the stage 16 and the optical assembly 14 including the first optical arrangement 22 and the second optical arrangement 24. The control computer 18 may be arranged to act as an operator console and master controller of the system. That is, all system interfaces with an operator and the user's facilities may be made through the control computer 18.

Commands may be issued to and status may be monitored from all other subsystems so as to facilitate completion of operator assigned tasks.

On the other hand, the electronics subsystem 19 may also be configured to interpret and execute the commands issued by control computer 18. The configuration may include capabilities for, but not limited to, digitizing the input from detectors, compensating these readings for variations in the incident light intensity, constructing a virtual image of the substrate surface based on the detected signals, detecting defects in the image and transferring the defect data to the control computer 18, accumulating the output of the interferometers used to track the stage 16, providing the drive for linear motors that move the stage 16 or components of the optical assembly 14, and monitoring sensors which indicate status. Control systems and stages are well know in the art and for the sake of brevity will not be discussed in greater detail. By way of example, a representative stage, as well as a representative controller may be found in U.S. Pat. No. 5,563,702, which is herein incorporated by reference. It should be understood, however, that this is not a limitation and that other suitable stages and control systems may be used.

As should be appreciated, the optical inspection system 10 can be arranged to perform several types of inspection, for example, transmitted light inspection, reflected light inspection and simultaneous reflected and transmitted inspection. In transmitted light inspection, light is incident on the substrate, a photomask for example, and the amount of light transmitted through the mask is detected. In reflected light inspection, the light reflecting from a surface of the substrate under test is measured. In addition to these defect detection operations, the system is also capable of performing line width measurement.

In most of the defect detection operations a comparison is made between two images. By way of example, the comparison may be implemented by the electronic subsystem 19 of FIG. 1. Broadly speaking, the detectors 42 generate scan signals, which are based on the measured light intensity, and send the scan signals to the electronic subsystem 19. The electronic subsystem 19, after receiving the scan signals, correspondingly compares the scan signals with reference signals, which are either stored in a database or determined in a current or previous scan.

More specifically, in die-to-die inspection mode, two areas of the substrate having identical features (dice) are compared with respect to each other and any substantial discrepancy is flagged as a defect. In the die-to-database inspection mode, a defect is detected by comparing the die under test with corresponding graphics information obtained from a computer aided database system from which the die was derived. In other defect detection operations, a comparison is made between two different modes of inspection. For example, in simultaneous reflected and transmitted inspection, a comparison is made between the light that is reflected off the surface of the substrate and light that is transmitted through the substrate. In this type of inspection the optical inspection system performs all of the inspection tasks using only the substrate to be inspected. That is, no comparisons are made between an adjacent die or a database.

Figure 2:
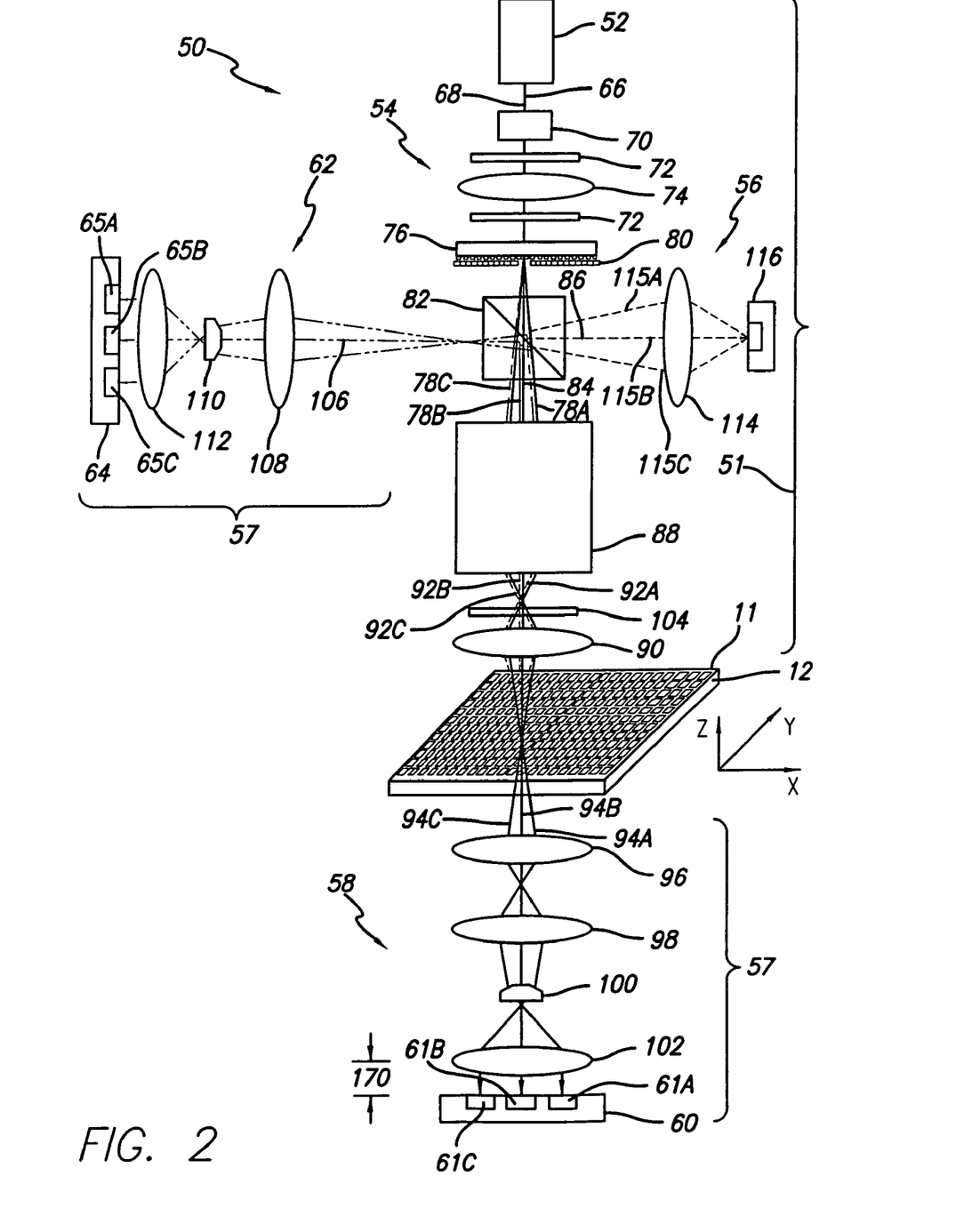
FIG. 2 is a detailed block diagram of an optical inspection system for inspecting the surface of a substrate, in accordance with one aspect of the present invention.

FIG. 2 is a detailed block diagram of an optical assembly 50 for inspecting the surface 11 of the substrate 12, in accordance with one embodiment of the present invention. By way of example, the optical assembly 50 may be the optical assembly 14 as described in FIG. 1. The optical assembly 50 generally includes a first optical arrangement 51 and a second optical arrangement 57, both of which may respectively correspond to the first optical arrangement 22 and the second optical arrangement 24 of FIG. 1. As shown, the first optical arrangement 51 includes at least a light source 52, inspection optics 54, and reference optics 56, while the second optical arrangement 57 includes at least transmitted light optics 58, transmitted light detectors 60, reflected light optics 62, and reflected light detectors 64.

The light source 52 is arranged for emitting a light beam 66 along a first path 68. The light beam 66 emitted by the light source 52, first passes through an acousto optic device 70, which is arranged for deflecting and focusing the light beam. Although not shown, the acousto optic device 70 may include a pair of acousto-optic elements, which may be an acousto-optic prescanner and an acousto-optic scanner. These two elements deflect the light beam in the Y-direction and focus it in the Z-direction. By way of example, most acousto-optic devices operate by sending an RF signal to quartz or a crystal such as $TeO_2$. The signal causes a sound wave to travel through the crystal. Because of the traveling sound wave, the crystal becomes asymmetric, which causes the index of refraction to change throughout the crystal. This change causes incident beams to form a focused traveling spot which is deflected in an oscillatory fashion.

When the light beam 66 emerges from the acousto-optic device 70, it then passes through a pair of quarter wave plates 72 and a relay lens 74. The relay lens 74 is arranged to collimate the light beam 66. The collimated light beam 66 then continues on its path until it reaches a diffraction grating 76. The diffraction grating 76 is arranged for flaring out the light beam 66, and more particularly for separating the light beam 66 into three distinct beams, which are designated 78A, 78B and 78C. In other words, each of the beams are spatially distinguishable from one another (i.e., spatially distinct). In most cases, the spatially distinct beams 78A, 78B and 78C are also arranged to be equally spaced apart and have substantially equal light intensities.

Upon leaving the diffraction grating 76, the three beams 78A, 78B and 78C pass through an aperture 80 and then continue along path 68 until they reach a beam splitter cube 82. The beam splitter cube 82 (working with the quarter wave plates 72) is arranged to divide the beams into paths 84 and 86. Path 84 is used to distribute a first light portion of the beams to the substrate 12 and path 86 is used to distribute a second light portion of the beams to the reference optics 56. In most embodiments, most of the light is distributed to the substrate 12 along path 84 and a small percentage of the light is distributed to the reference optics 56 along path 86. It should be understood, however, that the percentage ratios may vary according to the specific design of each optical inspection system. In brief, the reference optics 56 include a reference collection lens 114 and a reference detector 116. The reference collection lens 114 is arranged to collect and direct the second portion of the beams, now designated 115A-C, on the reference detector 116. As should be appreciated, the reference detector 116 is arranged to measure the intensity of the light. Although not shown in FIG. 2, the reference detector 116 is generally coupled to an electronic subsystem such as the electronic subsystem 19 of FIG. 1 such that the data collected by the detector can be transferred to the control system for analysis. Reference optics are generally well known in the art.

The three beams 78A, 78B and 78C continuing along path 84 are received by a telescope 88. Although not shown, inside the telescope 88 there are a several lens elements that redirect and expand the light. In one embodiment, the telescope is part of a telescope system that includes a plurality of telescopes rotating on a turret. For example, three telescopes may be used. The purpose of these telescopes is to vary the size of the scanning spot on the substrate and thereby allow selection of the minimum detectable defect size. More particularly, each of the telescopes generally represents a different pixel size. As such, one telescope may generate a larger spot size making the inspection faster and less sensitive (e.g., low resolution), while another telescope may generate a smaller spot size making inspection slower and more sensitive (e.g., high resolution).

From the telescope 88, the beams 78A, 78B and 78C pass through an objective lens 90, which is arranged for focusing the beams 78A, 78B and 78C onto the surface 11 of the substrate 12. As the beams 78A-C intersect the surface 11 of the substrate 12 both reflected light beams 92A, 92B, and 92C and transmitted light beams 94A, 94B, and 94C may be generated. The transmitted light beams 94A, 94B, and 94C pass through the substrate 12, while the reflected light beams 92A, 92B, and 92C reflect off the surface 11 of the substrate 12. By way of example, the reflected light beams 92A, 92B, and 92C may reflect off of an opaque surfaces of the substrate, and the transmitted light beams 94A, 94B, and 94C may transmit through transparent areas of the substrate. The transmitted light beams 94 are collected by the transmitted light optics 58 and the reflected light beams 92 are collected by the reflected light optics 62.

With regards to the transmitted light optics 58, the transmitted light beams 94A, 94B, 94C, after passing through the substrate 12, are collected by a first transmitted lens 96 and focused with the aid of a spherical aberration corrector lens 98 onto a transmitted prism 100. As shown, the prism 100 has a facet for each of the transmitted light beams 94A, 94B, 94C that are arranged for repositioning and bending the transmitted light beams 94A, 94B, 94C. In most cases, the prism 100 is used to separate the beams so that they each fall on a single detector in the transmitted light detector arrangement 60. As shown, the transmitted light detector arrangement 60 includes three distinct detectors 61A-C, and more particularly a first transmission detector 61A, a second transmission detector 61B, and a third transmission detector 61C. Accordingly, when the beams 94A-C leave the prism 100 they pass through a second transmitted lens 102, which individually focuses each of the separated beams 94A, 94B, 94C onto one of these detectors 61A-C. For example, beam 94A is focused onto transmission detector 61A; beam 94B is focused onto transmission detector 61B; and beam 94C is focused onto transmission detector 61C. As should be appreciated, each of the transmission detectors 61A, 61B, or 61C is arranged for measuring the intensity of the transmitted light.

With regards to the reflected light optics 62, the reflected light beams 92A, 92B, and 92C after reflecting off of the substrate 12 are collected by the objective lens 90, which then directs the beams 92A-C towards the telescope 88. Before reaching the telescope 88, the beams 92A-C also pass through a quarter wave plate 104. In general terms, the objective lens 90 and the telescope 88 manipulate the collected beams in a manner that is optically reverse in relation to how the incident beams are manipulated. That is, the objective lens 90 re-collimates the beams 92A, 92B, and 92C, and the telescope 88 reduces their size. When the beams 92A, 92B, and 92C leave the telescope 88, they continue along path 84 (backwards) until they reach the beam splitter cube 82. The beam splitter 82 is arranged to work with the quarter wave-plate 104 to direct the beams 92A, 92B, and 92C onto a path 106.

The beams 92A, 92B, and 92C continuing on path 106 are then collected by a first reflected lens 108, which focuses each of the beams 92A, 92B, and 92C onto a reflected prism 110, which includes a facet for each of the reflected light beams 92A-C. The reflected prism 110 is arranged for repositioning and bending the reflected light beams 92A, 92B, 92C. Similar to the transmitted prism 100, the reflected prism 110 is used to separate the beams so that they each fall on a single detector in the reflected light detector arrangement 64. As shown, the reflected light detector arrangement 64 includes three individually distinct detectors 65A-C, and more particularly a first reflected detector 65A, a second reflected detector 65B, and a third reflected detector 65C. Of course, each detector may be packaged separately or together. When the beams 92A-C leave the prism 110, they pass through a second reflected lens 112, which individually focuses each of the separated beams 92A, 92B, 92C onto one of these detectors 65A-C. For example, beam 92A is focused onto reflected detector 65A; beam 92B is focused onto reflected detector 65B; and beam 92C is focused onto reflected detector 65C. As should be appreciated, each of the reflected detectors 65A, 65B, or 65C is arranged for measuring the intensity of the reflected light.

There are multiple inspection modes that can be facilitated by the aforementioned optical assembly 50. By way of example, the optical assembly 50 can facilitate a transmitted light inspection mode, a reflected light inspection mode, and a simultaneous inspection mode. With regards to transmitted light inspection mode, transmission mode detection is typically used for defect detection on substrates such as conventional optical masks having transparent areas and opaque areas. As the light beams 94A-C scan the mask (or substrate 12), the light penetrates the mask at transparent points and is detected by the transmitted light detectors 61A-C, which are located behind the mask and which measure the light of each of the light beams 94A-C collected by the transmitted light optics 58 including the first transmitted lens 96, the second transmitted lens 102, the spherical aberration lens 98, and the prism 100.

With regards to reflected light inspection mode, reflected light inspection can be performed on transparent or opaque substrates that contain image information in the form of chromium, developed photoresist or other features. Light reflected by the substrate 12 passes backwards along the same optical path as the inspection optics 54 but is then diverted by a polarizing beam splitter 82 into detectors 65A-C. More particularly, the first reflected lens 108, the prism 110 and the second reflected lens 112 project the light from the diverted light beams 92A-C onto the detectors 65A-C. Reflected light inspection may also be used to detect contamination on top of opaque substrate surfaces.

With regards to simultaneous inspection mode, both transmitted light and reflected light are utilized to determine the existence and/or type of a defect. The two measured values of the system are the intensity of the light beams 94A-C transmitted through the substrate 12 as sensed by transmitted light detectors 61A-C and the intensity of the reflected light beams 92A-C as detected by reflected light detectors 65A-C. Those two measured values can then be processed to determine the type of defect, if any, at a corresponding point on the substrate 12.

More particularly, simultaneous transmitted and reflected detection can disclose the existence of an opaque defect sensed by the transmitted detectors while the output of the reflected detectors can be used to disclose the type of defect. As an example, either a chrome dot or a particle on a substrate may both result in a low transmitted light indication from the transmission detectors, but a reflective chrome defect may result in a high reflected light indication and a particle may result in a lower reflected light indication from the same reflected light detectors. Accordingly, by using both reflected and transmitted detection one may locate a particle on top of chrome geometry which could not be done if only the reflected or transmitted characteristics of the defect was examined. In addition, one may determine signatures for certain types of defects, such as the ratio of their reflected and transmitted light intensities. This information can then be used to automatically classify defects.

By way of example, representative inspection modes including, reflected, transmitted and simultaneous reflected and transmitted modes, may be found in U.S. Pat. No. 5,563, 702, which is herein incorporated by reference. It should be understood, however, that these modes are not a limitation and that other suitable modes may be used.

Further details of the system of FIGS. 1 and 2 wherein the present invention may be employed may be found in U.S. patent application Ser. No. 09/636,124, filed Aug. 10, 2000, and U.S. patent application Ser. No. 09/636,129, filed Aug. 10, 2000, both assigned to the assignee of the present invention, the entirety of which are incorporated herein by reference. As may be appreciated to those skilled in the art, other systems and designs may be used to practice the present invention.

Transmitted and Reflected Processing

Figure 4:
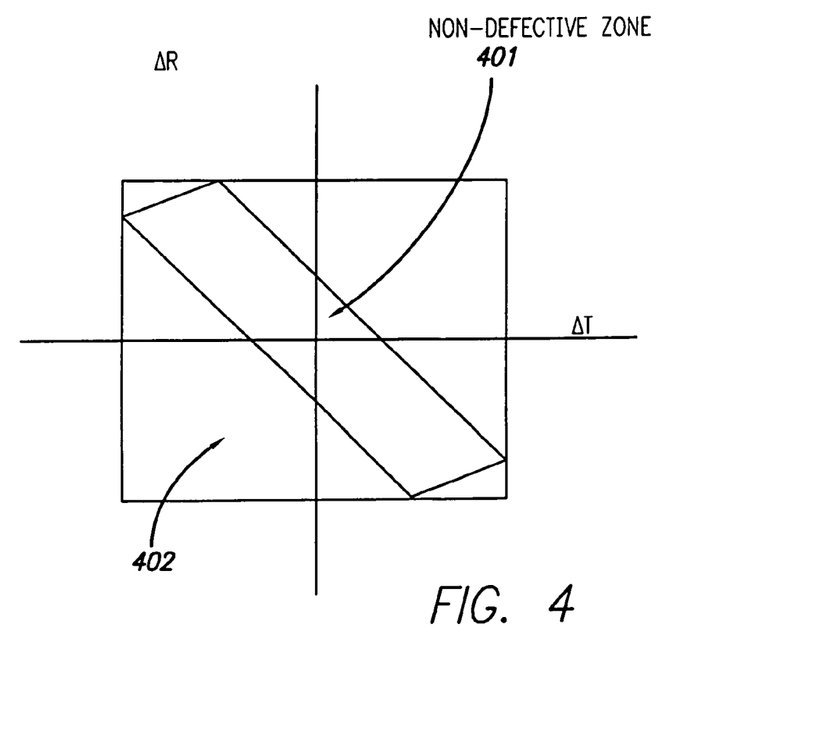
FIG. 4 represents modifications of the non-defective threshold.
Figure 5:
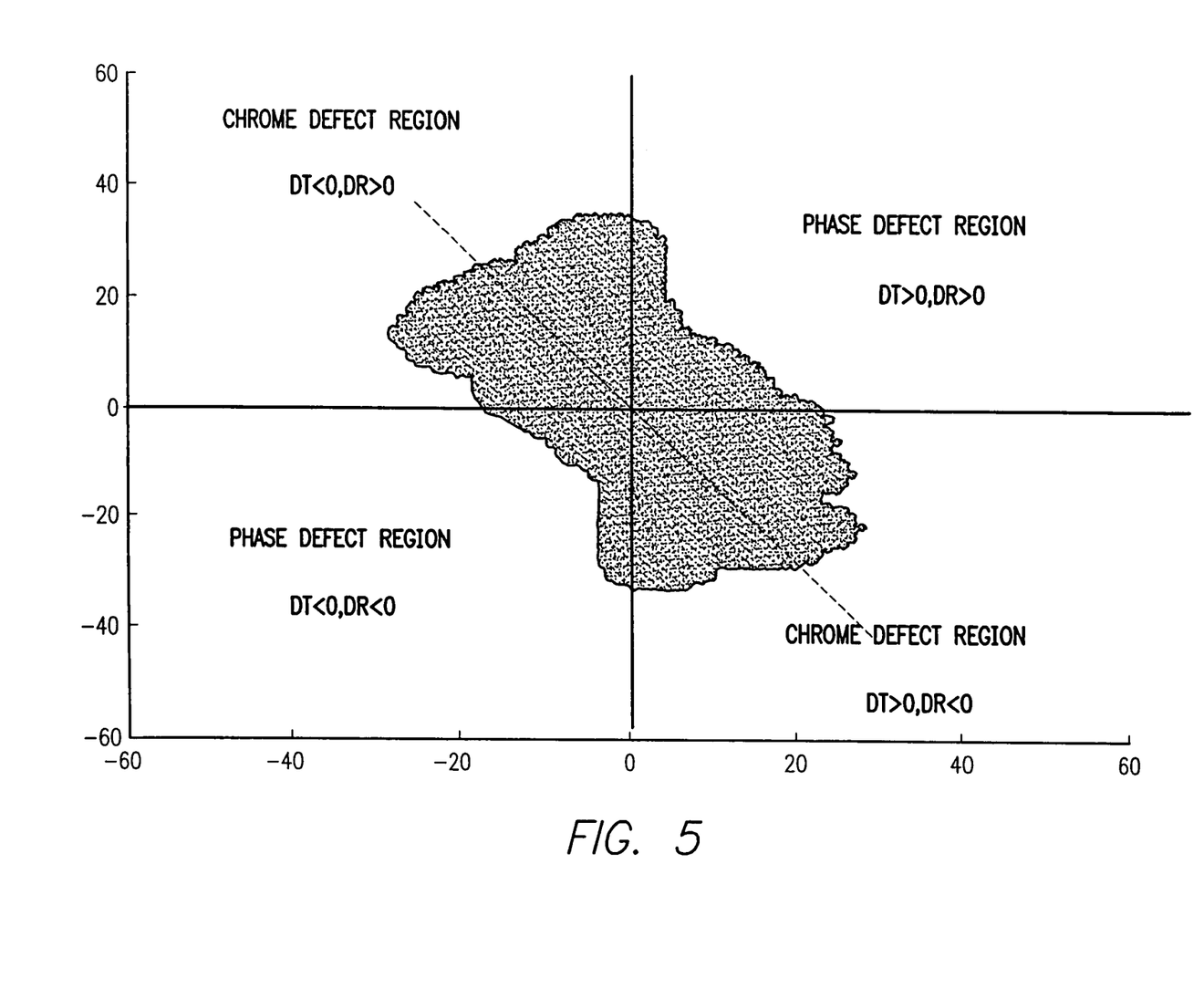
FIG. 5 is an expected ΔT-ΔR scan representation of a pair of images.

Transmitted light and reflected light exhibit reverse behavioral characteristics such that when transmitted light intensity decreases, reflected light intensity usually increases. Considering this phenomenon in the $\Delta T$-$\Delta R$ plane, $\Delta T$ and $\Delta R$ will follow the relationship that $\Delta T * \Delta R$ is less than zero. Phase errors, in contrast to chrome defects, typically exist when the transmitted and reflected light exhibit similar properties, such as when both transmitted and reflected differences are greater than or are both less than zero. The non-defective threshold is modified using these relationships as shown in FIG. 4, where modified non-defective zone 401 is bordered by removed region 402, representing the sensitivity increase over the $\Delta T$ and $\Delta R$ constant thresholds. In practice, after scanning test and reference images and subtracting transmitted and reflected pixel quantities, the result is as shown in FIG. 5. FIG. 5 is a $\Delta T$-$\Delta R$ scan representation of a pair of images, test and reference, where chrome defects generally exist when $\Delta T$ and $\Delta R$ have opposite signs, one positive and one negative. Phase defects exist where $\Delta T$ and $\Delta R$ have identical signs, i.e. where both $\Delta T$ is positive and $\Delta R$ is positive or where both $\Delta T$ is negative and $\Delta R$ is negative. From the roughly negative 45 degree sloping graphical representation, the area of likely defect locations can be more precisely assumed, drawn, and considered to more accurately assess the presence of defects.

Defect detection according to the present invention employs a two step process, a calibration step followed by a defect detection step. These processes or procedures may be embodied as part(s) of the control system 17, control computer 18, and/or electronics subsystem 19 of FIG. 1, or may be included in a separate processing subsystem not illustrated but interacting with the inspection optics design such that transmitted and reflected image representations may be received and processed according to the following description. Dual stage defect detection according to the present invention may be performed by hardware, such as an ASIC, software, firmware, or in a manner known to those skilled in the art.

In the present invention, an initial calibration step determines the non-defective region on the $\Delta T$-$\Delta R$ plane for a specific pair of dies, namely a test and reference die. This calibration generates a training set to represent the non-defective region on the $\Delta T$-$\Delta R$ plane. Multiple image pairs may be used to generate this calibration training set. In practice, one may select the pattern on the mask having the greatest density or most complicated pattern when generating the training set. Other parameters may be used to select calibration patterns used for developing the training set. Selection of the high density or most complicated pattern can, in certain circumstances, avoid certain false defects.

Figure 6:
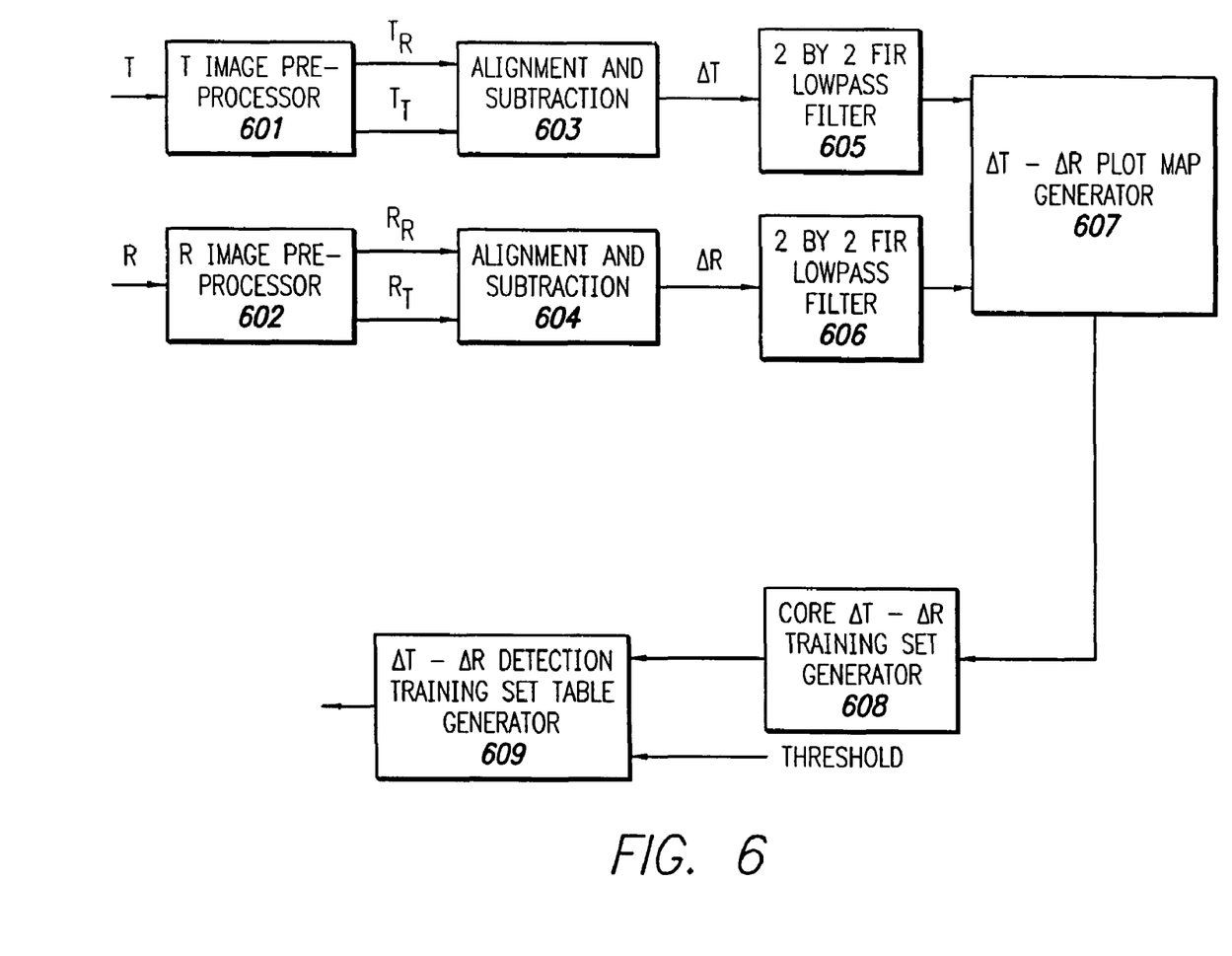
FIG. 6 represents the calibration performed by the present detection system using both transmitted and reflected images to produce a detection training set.

FIG. 6 represents the calibration functions performed by the detection system using both transmitted and reflected image data. From FIG. 6, the transmitted image (for both the test and reference specimens) is pre-processed at block 601 into a transmitted reference image and a transmitted test image. The reflected image (for both the test and reference specimens) is pre-processed at block 602 into a reflected test image and a reflected reference image. Preprocessing here includes obtaining fixed pixel subimages of the test and reference specimens, such as a 70 by 70 pixel, 120 by 120 pixel, 180 by 180 pixel, or other sized subimage of the specimens.

Fine sub-pixel alignment and subtraction blocks 603 and 604 align the test and reference images for both transmitted and reflected representations, resulting in a $\Delta T(i,j)$ for the transmitted images and a $\Delta R(i,j)$ for the reflected images. Alignment may be performed before subtraction in blocks 603 and 604. These aligned and subtracted values are passed through two 2 by 2 FIR (Finite Impulse Response) low pass filters 605 and 606, resulting in reduced noise $\Delta T(i,j)$ and $\Delta R(i,j)$ values. Use of either or both FIR lowpass filters is optional. Generally, if no significant false defect readings are expected or actually occur for a mask, the filter can optionally be overlooked.

The system generates a $\Delta T$-$\Delta R$ plot map using the $\Delta T$ and $\Delta R$ values at plot map generator 607. The system then generates a core $\Delta T$-$\Delta R$ training set at core training set generator 608. A threshold is applied along with the core training set from core training set generator 608 at detection training set table generator 609. Application of the threshold provides a buffer zone around the core $\Delta T$-$\Delta R$ training set, and the threshold may vary depending on circumstances. For example, a zero to five pixel border, or other sized border, may be applied around all pixels from the core $\Delta T$-$\Delta R$ training set to include close cases.

Figure 7:
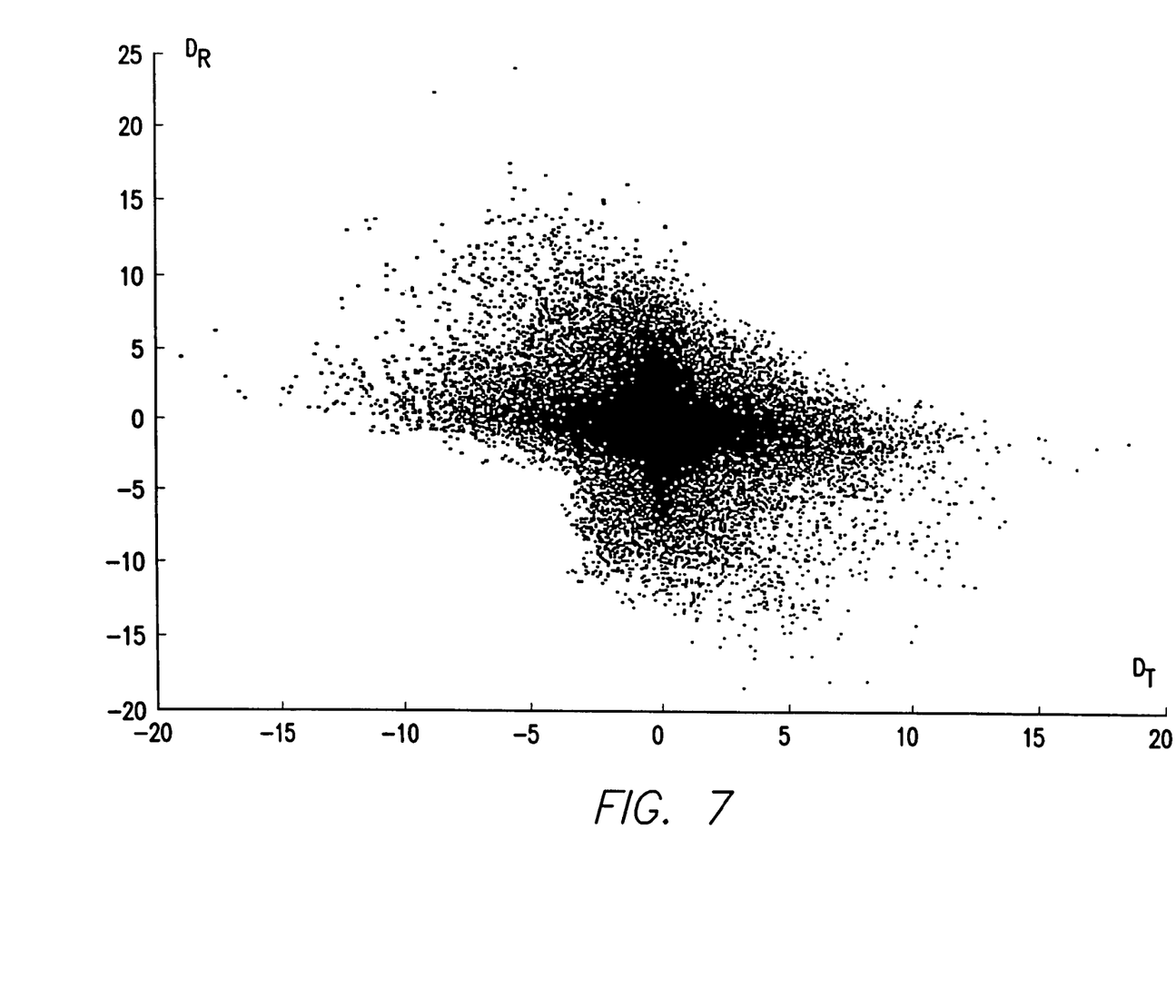
FIG. 7 illustrates a representative ΔT-ΔR plot as may be generated by the plot map generator.
Figure 8:
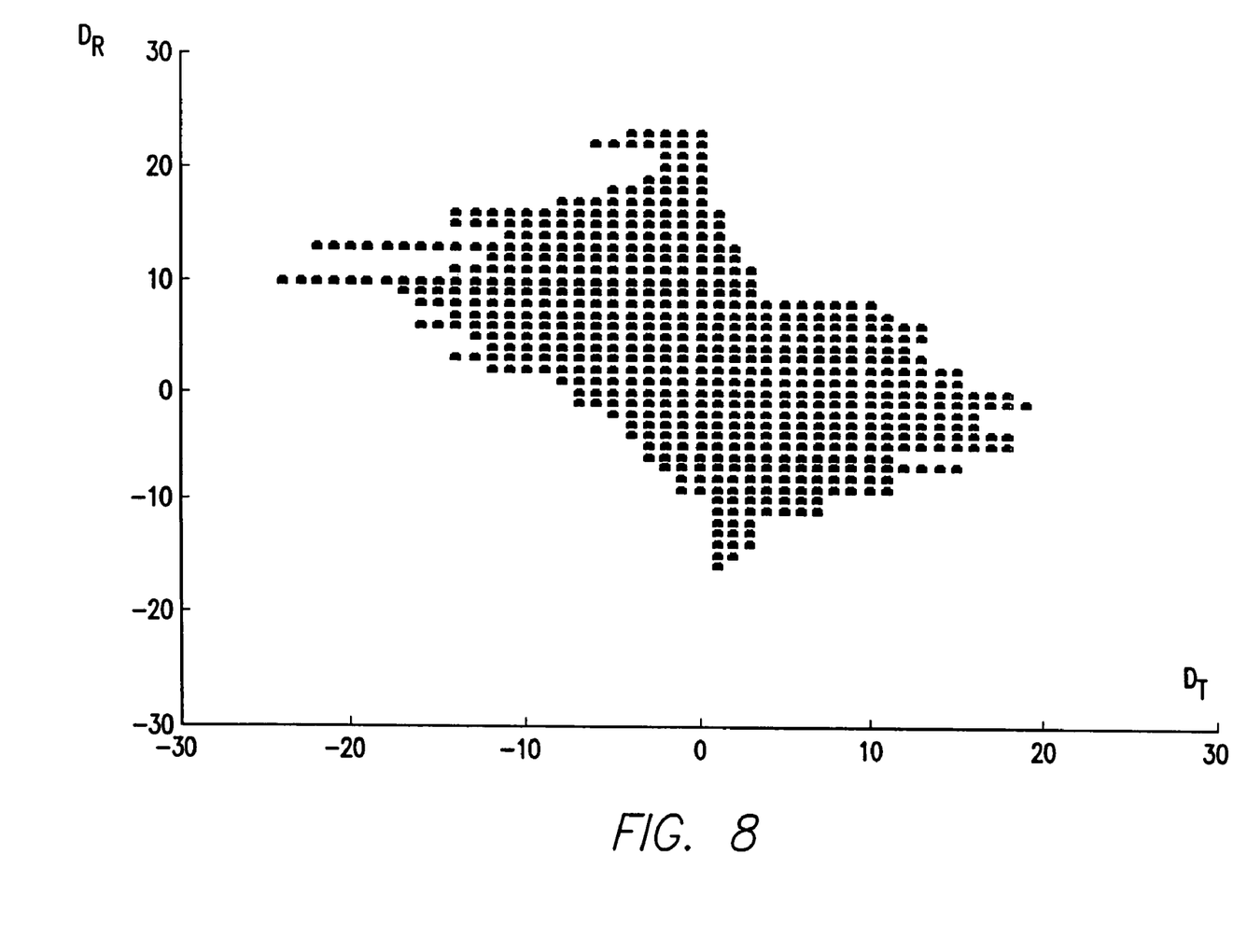
FIG. 8 shows a core ΔT-ΔR training set as may be generated by the core training set generator.
Figure 9:
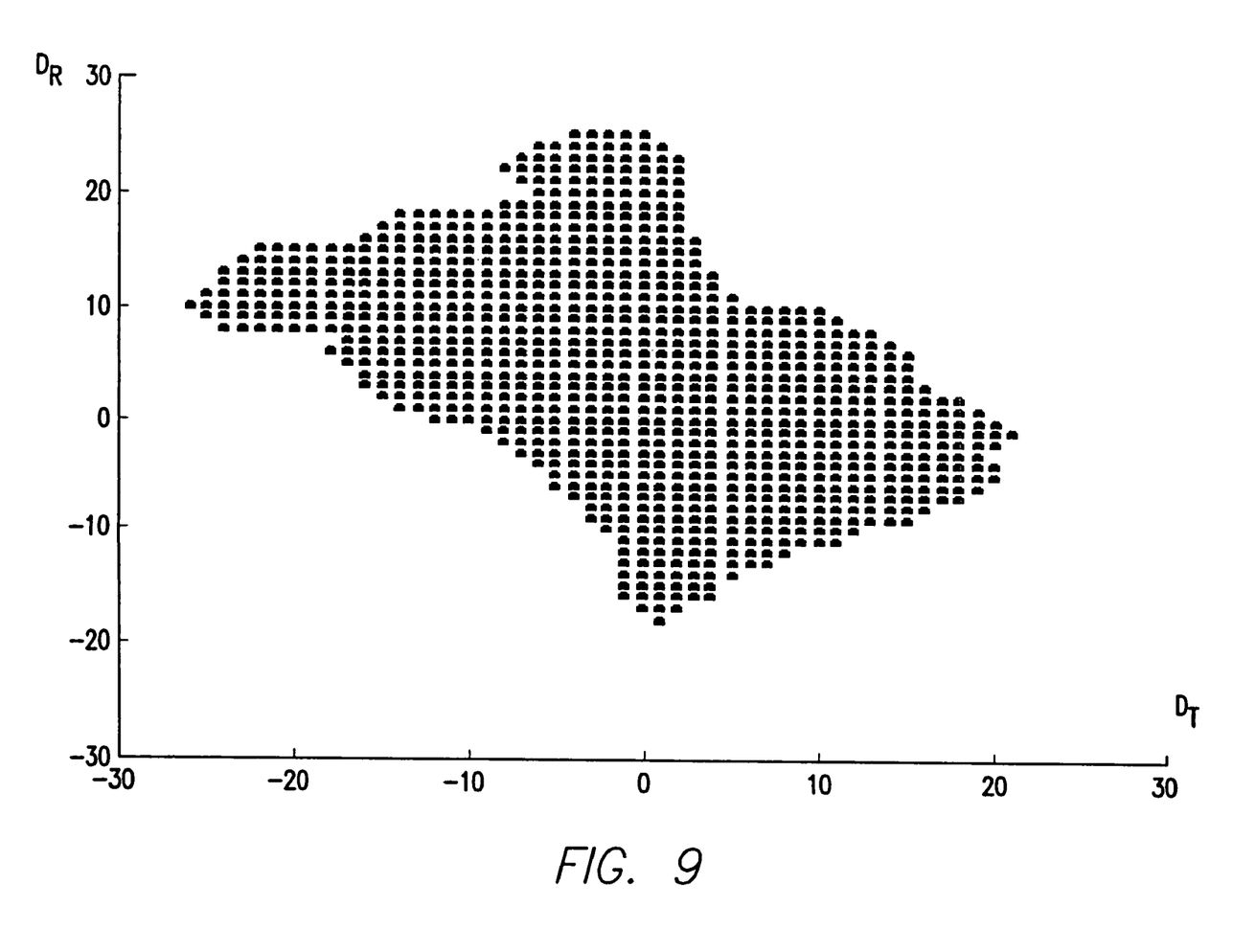
FIG. 9 presents an enhanced TR training set as may be generated by the detection training set generator.

A representative $\Delta T$-$\Delta R$ plot as may be generated by plot map generator 608 is illustrated in FIG. 7. A core $\Delta T$-$\Delta R$ training set as may be generated by core training set generator 608 is presented in FIG. 8. FIG. 9 presents an enhanced or dilated TR training set as may be generated by detection training set generator 609. As compared with the core training set of FIG. 8, certain stray artifacts are buffered using detection training set generator 609, and the pixels of FIG. 9 represent the non-defective region used for subsequent processing. The non-defective region resulting from the detection training set generator 609 may be converted to a look up table for reference purposes.

Figure 10:
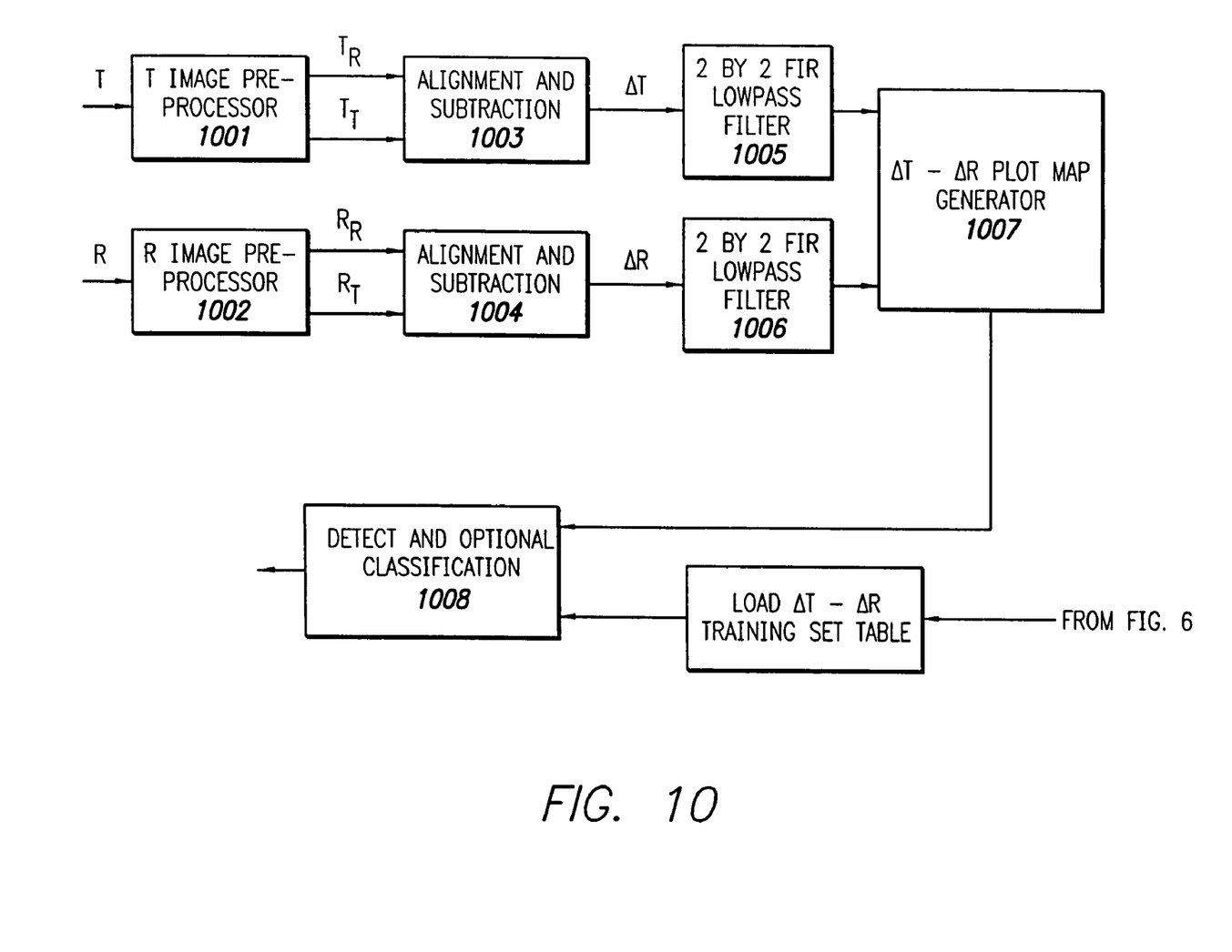
FIG. 10 illustrates the defect detection processor of the present invention.

Defect detection processes four images: $T_T(i,j)$, the transmitted image from the test die; $T_R(i,j)$, the reflected image from the test die; $R_T(i,j)$, the transmitted image from the reference die; and $R_R(i,j)$, the reflected image from the reference die. i and j vary from 1 to the number of pixels in each direction within the image. FIG. 10 illustrates the defect detection processor. From FIG. 10, test die image preprocessor 1001 processes the test die into test reflected and test transmitted representations. Reference die image preprocessor 1002 processes the reference die into reference reflected and reference transmitted representations. These four components are then aligned and subtracted in alignment and subtraction blocks 1003 and 1004 to produce $\Delta T$ and $\Delta R$ values, which are passed to two 2 by 2 FIR filters 1005 and 1006 for noise reduction. Again, use of either or both of these lowpass FIR filters is optional. Generally, use of each lowpass FIR filter at this stage depends on whether the filter was applied on the calibration stage, i.e. was used in the design of FIG. 6. The ΔT and ΔR components are used to generate a ΔT-ΔR plot map at plot map generator 1007. The generated ΔT-ΔR plot map is compared against the ΔT-ΔR training set table generated at detection training set table generator 609 in defect detection and classification block 1008. If the ΔT-ΔR plot from plot map generator 1007 includes pixels outside of the pixels in the training set representation provided by detection training set generator 609, or outside the non-defective region, those pixels are flagged as defective. After the system processes all pixels for all images, all defects are identified for potential post processing. Post processing may entail an operator reviewing the regions to determine the acceptability of the region and/or presence of a defect, or automated review of the particular area, or any method of defect review known in the art. Post processing may alternately entail computing the number of defects or potential defects and considering the sample bad if the number of defects exceeds a predetermined threshold. Post processing is an optional part of the present procedure.

While the invention has been described in connection with specific embodiments thereof, it will be understood that the invention is capable of further modifications. This application is intended to cover any variations, uses or adaptations of the invention following, in general, the principles of the invention, and including such departures from the present disclosure as come within known and customary practice within the art to which the invention pertains.

What is claimed is:

1. A method for inspecting a specimen, the method performed using a processing device and comprising:
   performing a transmitted energy inspection of at least one specimen;
   performing a reflected energy inspection of the at least one specimen;
   computing a map representing results from the transmitted energy inspection and the reflected energy inspection of the at least one specimen; and
   assessing differences between the map and known data, said known data comprising a training set representing previously scanned reference specimen attributes within at least one expected defect region.

2. The method of claim 1, wherein the known data is computed based on a transmitted energy calibration inspection and a reflected energy calibration inspection of a plurality of calibration specimens prior to said performing the transmitted energy inspection and said performing the reflected energy inspection.

3. The method of claim 2, wherein said known data computing comprises generating a core training set and applying a threshold to the core training set.

4. The method of claim 3, wherein said known data computing further comprises generating a calibration plot map prior to generating the core training set.

5. The method of claim 3, wherein computing the known data establishes a pixilated expected non defective region.

6. The method of claim 2, further comprising filtering the transmitted energy calibration inspection and reflected energy calibration inspection prior to computing the known data.

7. The method of claim 6, wherein said transmitted energy calibration inspection and reflected energy calibration inspection filtering comprises lowpass filtering.

8. The method of claim 1, wherein the transmitted energy inspection and the reflected energy inspection are performed at different times.

9. The method of claim 1, wherein the reflected energy inspection is performed before the transmitted energy inspection.

10. A method for inspecting a specimen, the method performed using a processing device and comprising:
    performing a transmitted energy-reflected energy inspection of the specimen;
    computing a map based on the transmitted energy-reflected energy inspection of the specimen and transmitted and reflected information from an alternate baseline specimen; and
    determining anomalies on the specimen based on the map in combination with known data comprising a training set representing previously scanned reference specimen attributes within at least one expected defect region and selectively making the anomalies determined available for review.

11. The method of claim 10, further comprising computing known data based on a transmitted energy-reflected energy inspection of a calibration specimen and transmitted-reflected energy from a baseline specimen prior to said determining.

12. The method of claim 11, further comprising performing a transmitted-reflected energy calibration inspection of the calibration specimen prior to computing the known data.

13. The method of claim 11, wherein the transmitted-reflected energy from the baseline specimen comprises baseline specimen data stored in a database.

14. The method of claim 11, wherein transmitted-reflected energy from the alternate baseline specimen comprises alternate baseline specimen data stored in a database.

15. The method of claim 11, wherein said known data computing comprises generating a core training set and applying a threshold to the core training set.

16. A system for inspecting a specimen, comprising:
    a defect detector; and
    a table generator configured to interact with the defect detector;
    wherein the defect detector receives a combined specimen representation from the table generator comprising a training set representing previously scanned reference specimen attributes within at least one expected defect region and a transmitted/reflected energy representation of the specimen and the defect detector is configured to determine differences therebetween.

17. The system of claim 16, wherein the combined specimen representation comprises a calibration transmitted energy and calibration reflected energy representation of at least one specimen.

18. The system of claim 16, wherein the table generator comprises:
    a baseline plot map generator that that receives transmitted-reflected energy characterizations representing multiple specimens and generates a map;
    a core training set generator that generates a core pixilated training set based on the map; and
    a detection training set table generator that receives the core pixilated training set and applies a threshold to the core pixilated training set to the core pixilated training set.

19. The system of claim 16, wherein said defect detector further comprises:
    a subject specimen plot map generator that receives transmitted-reflected energy characterizations representing multiple specimens and generates a subject specimen difference plot map;

a loader for loading the combined calibration transmitted-reflected energy difference representation; and a detector that receives the subject specimen plot map and determines potential defects.

20. The system of claim 19, wherein said training set table generator further comprises:

a preprocessor to divide transmitted-reflected energy into transmitted and reflected components; and an alignment and subtraction element that aligns the transmitted and reflected components and establishes a difference for transmitted and reflected components.

21. A method for inspecting a specimen, comprising:

performing an initial calibration using transmitted and reflected images of at least one specimen to form initial calibration results within at least one identified zone;

using initial calibration results in combination with transmitted-reflected data from the specimen to form a combined transmitted-reflected energy map usable to assess anomalies on the specimen; and selectively making assessed anomalies available for review.

22. The method of claim 21, wherein the combined transmitted-reflected energy map employs information compiled from a transmitted energy inspection and the a reflected energy inspection of the at least one specimen.

23. The method of claim 21, wherein the combined transmitted-reflected energy map comprises data taken from a test specimen and a reference specimen.

24. A system for inspecting a specimen, comprising:

means for performing a transmitted and reflected inspection of a specimen and generating a plot map of the transmitted and reflected inspection of the specimen using known data comprising a training set representing previously scanned reference specimen attributes within at least one expected defect region; and means for detecting defects based on the plot map.

25. The system of claim 24, wherein the means for performing and generating comprise a processor configured to employ transmitted and reflected data from a test specimen and transmitted and reflected data from a reference specimen in generating the plot map.

* * * * *